(12) United States Patent
Missaglia

(10) Patent No.: US 10,254,208 B2
(45) Date of Patent: Apr. 9, 2019

(54) METHOD FOR ANALYZING BLOOD SAMPLES FOR DETECTION OF PATHOLOGIES

(71) Applicant: GRADEMI BIOTECH S.R.L., Bologna (BO) (IT)

(72) Inventor: Adelio Missaglia, Monza (IT)

(73) Assignee: GRADEMI BIOTECH S.R.L., Bologna (IT)

( * ) Notice: Subject to any disclaimer, the term of this patent is extended or adjusted under 35 U.S.C. 154(b) by 38 days.

(21) Appl. No.: 15/117,644

(22) PCT Filed: Feb. 3, 2015

(86) PCT No.: PCT/IB2015/050812
§ 371 (c)(1),
(2) Date: Aug. 9, 2016

(87) PCT Pub. No.: WO2015/118443
PCT Pub. Date: Aug. 13, 2015

(65) Prior Publication Data
US 2016/0349166 A1  Dec. 1, 2016

(30) Foreign Application Priority Data

Feb. 10, 2014  (IT) ............................... MI2014A0182

(51) Int. Cl.
*G01N 15/05* (2006.01)
*G01N 33/49* (2006.01)
*G01N 15/00* (2006.01)

(52) U.S. Cl.
CPC ........... *G01N 15/05* (2013.01); *G01N 33/491* (2013.01); *G01N 2015/0073* (2013.01)

(58) Field of Classification Search
CPC .......... G01N 15/05; G01N 2015/0073; G01N 2015/008; G01N 2015/0084; G01N 33/49;
(Continued)

(56) References Cited

U.S. PATENT DOCUMENTS 4,848,900 A * 7/1989 Kuo ....................... G01N 15/05
356/39
8,647,886 B1 * 2/2014 Sacchetti ............... G01N 21/51
435/2

FOREIGN PATENT DOCUMENTS

WO          01/23864 A1     4/2001

OTHER PUBLICATIONS

Voeikov, V.L. et al., "Blood as an Active Colloidal System: The Nonlinear Nature of Erythrocyte Sedimentation in Whole Blood Revealed by Video Recording with High Spatial-Temporal Resolution", Moscow University Chemical Bulletin, Allerton Press, Inc., Heidelberg, vol. 66, No. 4, Oct. 6, 2011, (Oct. 6, 2011), pp. 259-264, XP019961393, ISSN: 1935-0260, D01: 10.3103/S0027131411040092.
(Continued)

*Primary Examiner* — Maureen Wallenhorst
(74) *Attorney, Agent, or Firm* — Pearne & Gordon LLP

(57) ABSTRACT

A method for analyzing blood samples, including the steps of: preparing a blood sample (1) within a respective container (2) provided with an anticoagulant substance; measuring the rate (V) at which the corpuscular components (1a) contained in the blood sample (1) sediment on the bottom of the container (2), the rate (V) being measured over a predetermined time period (T); detecting, within the time period (T), at least one sedimentation trend (A1, A2, A3) representative of steps of aggregation of the corpuscular components (1a); and comparing the detected sedimentation
(Continued)

trend (A1, A2, A3) with at least one reference parameter (P1, P2, P3) representative of at least one given pathology.

8 Claims, 4 Drawing Sheets

(58) Field of Classification Search
CPC ... G01N 33/4905; G01N 33/491; G01N 33/86
USPC ..... 436/63, 69, 70, 164, 176; 422/73, 82.05, 422/82.09; 435/13; 73/61.65, 61.69; 600/369, 370
See application file for complete search history.

(56) References Cited

OTHER PUBLICATIONS

Voeikov, Vladimir L. et al., "Computerised video-enhanced high temporal resolution of erythrocytes sedimentation rate (ESR-graphy) reveals complex dynamic and self-organising properties of whole blood", Procedings of SPIE, vol. 3923, May 30, 2000, (May 30, 2000), pp. 32-43, XP055112474, ISSN: 0277-786X, D01: 10.1117/12.387143.

Holley, L. et al., "Influence of fibrinogen and haematocrit on erythrocyte sedimentation kinetics", Biorheology, Elsevier Science Ltd., Oxford, GB, vol. 36, No. 4, Jan. 1, 1999, (Jan. 1, 1999), pp. 287-297, XP009175126, ISSN: 0006-355X.

Fabry, T.L., "Mechanism of erythrocyte aggregation and sedimentation", Blood, Nov. 1, 1987, (Nov. 1, 1987), pp. 1572-1576, XP055112465, United States, Retrieved from the Internet: URL:http://bloodjournal.hematologylibrary.org/cgi/content/abstract/70/5/1572 [retrieved on Apr. 7, 2014].

Cab-Cauich, Cesar et al., "Monitoring of blood sedimentation by a multiplexed light transmission method", Review of Scientific Instruments, AIP, Melville, NY, US, vol. 77, No. 4, Apr. 3, 2006, (Apr. 3, 2006), pp. 44301-044301, XP012093002, ISSN: 0034-6748, D01: 10.1063/1.2188847.

\* cited by examiner

METHOD FOR ANALYZING BLOOD SAMPLES FOR DETECTION OF PATHOLOGIES

TECHNICAL FIELD

The present invention relates to a method for analyzing blood samples.

In particular, the present invention relates to a method for evaluating the presence of pathologies in a subject from whom a blood sample is taken for analysis.

As is well known, blood samples can be examined and analyzed using different methods, all aimed at evaluating the health conditions of the subject concerned.

Such methods can be of a specific type, in which the pathology a subject may be affected by is determined with good precision, or else of a non-specific type, in which only an indication is given as to the possible presence of a pathology in the subject.

In the former case, specific tests are generally conducted in a laboratory using equipment and processors capable of evaluating and examining the composition of the blood in order then to determine any factors in the blood sample indicating problems or pathologies. In this case a specialized physician examines the blood sample and subsequently derives a clinical picture.

This type of analysis, though capable of precisely determining the presence of a specific pathology, has major drawbacks due mostly to the complexity of the analyses.

In fact, the blood sample is analyzed by means of particular equipment that is structurally complicated and costly and used only by specialized personnel in a laboratory setting. It is therefore impossible to have an evaluation of the blood sample within a short time and at a low cost.

For this reason, especially if it is not determined whether or not a pathology is present, this type of analysis proves to be disadvantageous in terms of the times and costs of performing it.

To overcome this drawback, use is made of non-specific tests able to provide an estimate, within a limited time and at a low cost, concerning the presence of an abnormal condition in the subject.

The most common and widely used non-specific test is the erythrocyte sedimentation rate (ESR) test, which is a measure of the speed at which red blood cells separate from plasma and settle on the bottom of a blood sample container.

The erythrocyte sedimentation rate is essentially conditioned by the characteristics of the plasma (in particular its protein composition) and the characteristics of the red blood cells (shape, number, tendency to aggregate, etc.).

This test is easy to perform, inexpensive and fast and, despite its non-specificity, it can indicate whether or not a pathology is present; the latter can be precisely identified by performing further tests of a specific type.

In particular, the erythrocyte sedimentation rate is measured by means of suitable devices, either manual or automatic, such as, for example, the devices described in international patent application WO 2001/23864, which are capable of measuring the sedimentation rate of the corpuscular components of blood (red and white blood cells and platelets).

The measured rate is then compared with a reference parameter to establish whether the subject is healthy or may be affected by any current pathologies.

Advantageously, the test is performed in a short time with simple devices that can also be used by non-specialized personnel as a first screening to determine whether it is necessary to proceed with the performance of other diagnostic tests.

The method generally used to analyze the erythrocyte sedimentation rate is the Westergren method, in which the blood sample is rendered non-coagulable by adding sodium citrate and allowed to sediment in a glass tube graduated in millimeters at a controlled temperature.

The glass container is then placed in special housing compartments fashioned in the above-mentioned known devices. Such devices are equipped with optical sensors capable of reading the speed at which the corpuscular components fall over a pre-determined time and of providing the values of the sedimentation rate via suitable management software.

The test is based on the tendency of erythrocytes (red blood cells) to remain in suspension if they remain separated from one another. In this case there is very little (slow) sedimentation, indicating that the blood sample belongs to a healthy subject.

If, on the other hand, the erythrocytes aggregate and form cellular clumps (called rouleaux), they will fall more rapidly to the bottom of the glass tube, thus indicating the presence of a pathology in the blood sample.

This phenomenon is due to the negative electrical charges present on the outer membrane of the erythrocytes which repel one another, tending to block the phenomenon of agglomeration (rouleaux formation).

The ability of the red blood cells to repel one another is reduced if, for example, there is a current inflammation (presence of proteins, particularly C-reactive protein, fibrinogen IgM etc.) which reduces the negative charge on the membrane.

In this case, the red blood cells tend to adhere to one another, forming agglomerates (clumps of red blood cells) which deposit more quickly on the bottom of the test tube, as they are heavier.

This test method, too, however, poses major drawbacks.

In fact, as specified above, the erythrocyte sedimentation rate test is not able to provide any information in a specific manner as to the ongoing pathology.

For this reason, utilization of this method remains very limited and it is of little use in the case of an in-depth evaluation of the health conditions of a subject.

Moreover, if the erythrocyte sedimentation rate test indicates the presence of a pathology, specific examinations will in any case have to be carried out, with a consequent increase in the times and costs of performing a complete analysis which can provide sufficient information about the subject's health conditions.

In this context, the technical task at the basis of the present invention is to propose a method for analyzing blood samples which overcomes the aforementioned drawbacks of the prior art.

In particular, it is an object of the present invention to provide a method for analyzing blood samples that is capable of furnishing specific information as to the presence of pathologies in a blood sample within a limited time and at a limited cost.

In particular, it is an object of the present invention to provide a method for analyzing blood samples capable of specifying types of pathologies without there being any need to examine the blood sample diagnostically.

A further object of the present invention is to provide a method for analyzing blood samples that can be implemented in a simple manner, also by non-specialized personnel.

Finally, it is an object of the present invention to provide a method for analyzing blood samples that can be implemented without setting up any specific equipment.

The stated technical task and the specified objects are substantially achieved by a method for analyzing blood samples, comprising the technical features set forth in one or more of the appended claims.

Additional features and advantages of the present invention will become more apparent from the approximate, and hence non-limiting, description of a preferred but non-exclusive embodiment of a method for analyzing blood samples, as schematically illustrated in the appended figures, in which.

Figure 1:
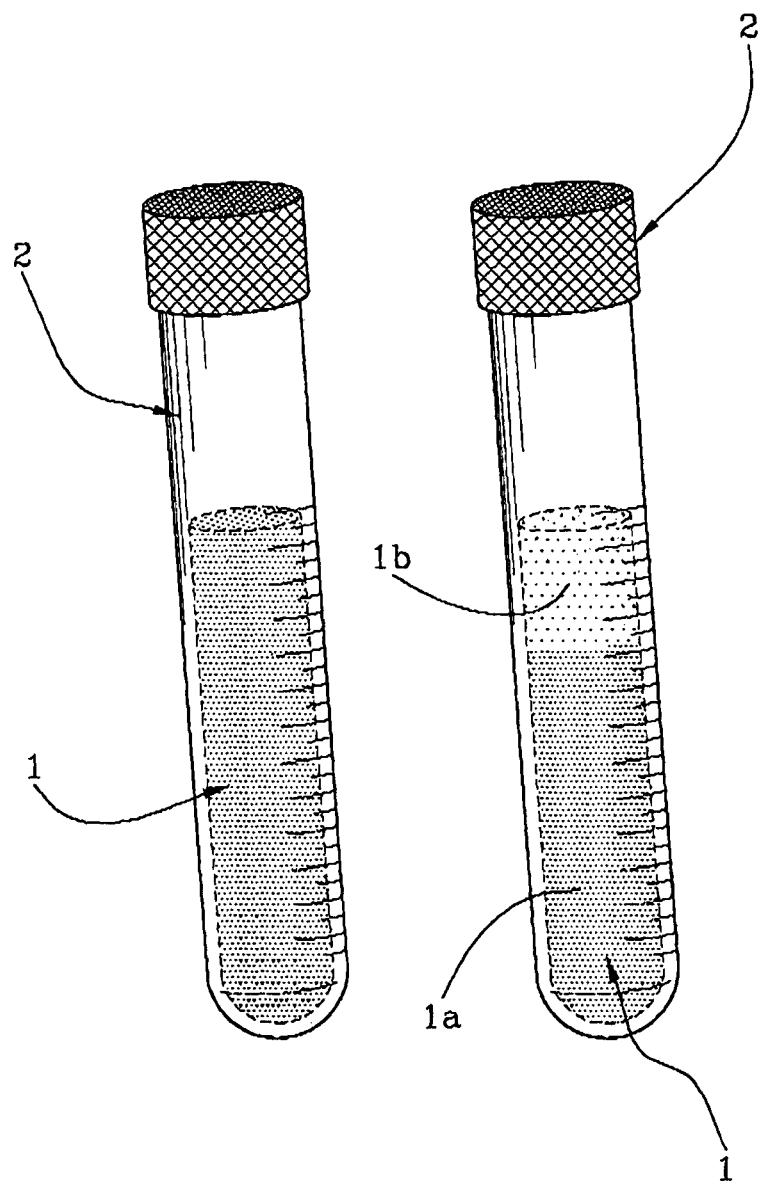
FIG. 1 shows a perspective view of blood samples contained in respective test tubes and in respective sedimentation conditions.

The method of the present invention is carried out, as illustrated in FIG. 1, by preparing a blood sample 1 inside a respective container 2. The container 2 preferably consists in a test tube graduated in millimeters, made of glass or another transparent material, in which an anticoagulant substance, preferably sodium citrate, has been previously added inside the container 2.

The blood sample 1 is then allowed to sediment, with the test tube set in a predetermined position, in order to be able to measure the rate V at which the corpuscular components 1a contained in the blood sample 1 settle on the bottle of the container 2.

The rate V is measured over a predetermined period of time T, which can be, for example, 10 minutes.

Advantageously, the rate V is measured by means of an electronic device for measuring the erythrocyte sedimentation rate—which is not described or illustrated herein, as it is of a known type and not part of the present invention—equipped with suitable optical sensors capable of measuring the speed at which the corpuscular components 1a (red and white blood cells and platelets) fall, that is, the time it takes them to separate from the plasma 1b. The test tube is thus inserted in a respective test seat of the device for measuring the erythrocyte sedimentation rate, in which the optical screening is carried out to determine the rate V over the predetermined time T.

The measured rate V is then compared with a reference rate indicative of whether or not a pathology is present.

In other words, the reference value determines the limit below which the measured rate V must fall in order to determine that the blood sample 1 belongs to a healthy subject.

In this case, in fact, the red blood cells remain in suspension for a longer time, lengthening the sedimentation process (fall toward the bottom of the container 2). This behaviour is due to the presence of negative charges on the surface membrane of the red blood cells, which tend to repel one another, avoiding the agglomeration thereof.

In contrast, in the event that the measured rate V is above the reference value, the presence of a pathology is determined. In this situation, any inflammations present in the blood favour the agglomeration of the red blood cells (as a result of the loss of the negative charge), which fall quickly toward the bottom of the test tube, thus reducing the sedimentation times.

In general, the reference value is established as 20 mm/h in women and 15 mm/h in men.

The management software of the device thus estimates whether the blood sample 1 reveals pathologies or not.

In this case, a sedimentation trend A1, A2, A3 representative of steps of aggregation of the corpuscular components 1a is measured within the time period T.

This step is carried out by reading, in at least one moment M1, M2 or M3 of the time period T, the formation of agglomerates of the corpuscular components 1a and the fall thereof in the plasma 1b contained in the blood sample 1.

In particular, the sedimentation trend A1, A2, A3 is represented by a curve (FIGS. 2 and 4) obtained by reading the formation of agglomerates and the fall thereof in the plasma for each moment that occurs sequentially along the whole time period T.

Figure 4:
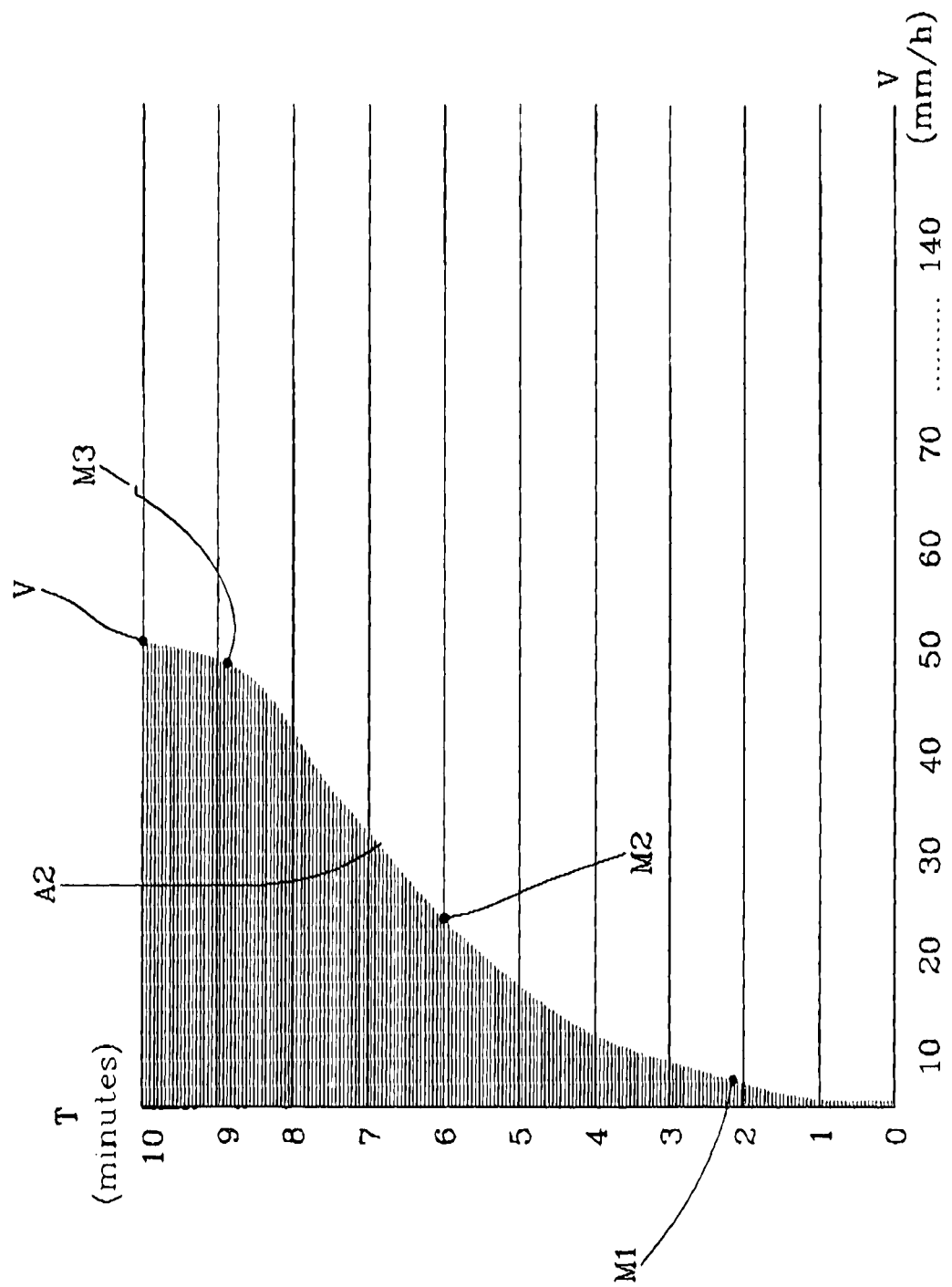
FIG. 4 shows a diagram that represents the way in which the sedimentation trend of a respective blood sample is drawn.

As is illustrated in FIG. 4, the reading moments are represented by predetermined time intervals, generally one reading every two seconds, in which the rate values are plotted. Taken together, these moments, which are graphically represented by means of mutually parallel segments extending as far as the measured rate, thus write the aforesaid curve representative of the sedimentation trend A1, A2, A3.

Figure 2:
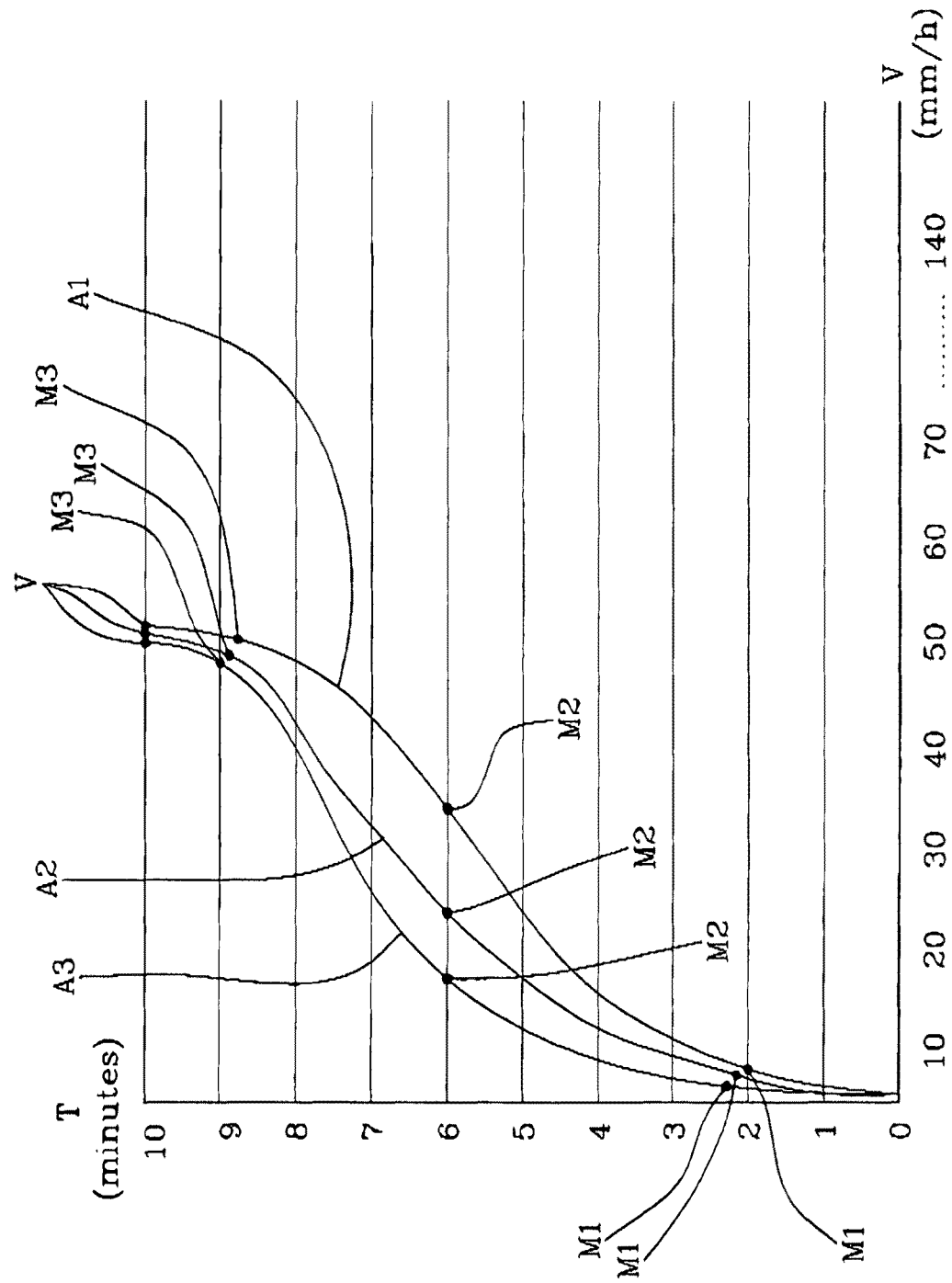
FIG. 2 shows diagrams which represent the sedimentation trends of different blood samples.
Figure 3:
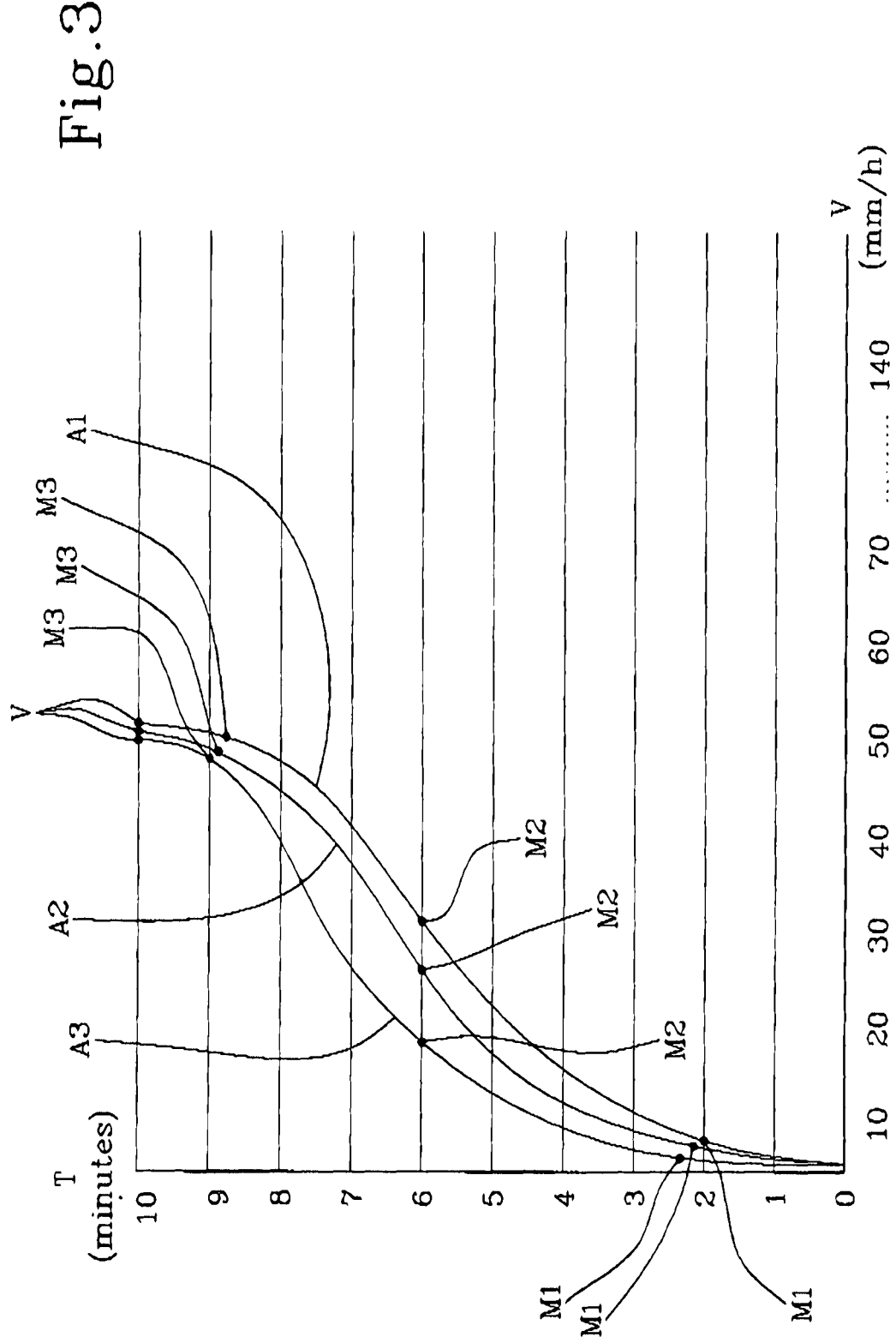
FIG. 3 shows diagrams of different reference sedimentation trends corresponding to specific pathologies.

It should be noted in particular that in FIG. 2 three curves A1, A2, A3 are represented by way of non-limiting example, each curve belonging to a sedimentation trend of respective blood samples.

It is illustrated, again by way of example, that each blood sample has the same rate V over the unit of time T (about 50 mm/h).

However, the sedimentation trends are different from one another, since each sedimentation trend A1, A2, A3 exhibits a specific curve.

In this respect, it should be specified that the sedimentation occurs in three steps: the first step is determined by the formation of aggregates; in the second step, a further aggregation of the cellular clumps (rouleaux) takes place; finally, in the third step an acceleration of sedimentation occurs, so that the aggregates accumulate on the bottom of the container 2.

These steps, which can take place differently depending on the various pathologies present in the blood sample, thus determine the difference in the respective sedimentation curves.

In fact, for each pathology, the corpuscular bodies 1a exhibit a specific behaviour (deriving from the loss of the negative charge of the red blood cells) in their ability to aggregate and therefore the way in which the sedimentation occurs.

For this reason, the sedimentation diagrams can be different from one another, though with identical sedimentation rates, or else they can have similar reaction times but different final values. Furthermore, the curves can provide indications about the presence of different points of aggregation or a different curve amplitude, the rates V being equal (as in the case illustrated in FIG. 2).

The plasma 1b, whose components are more numerous than in the corpuscular body 1a, also tends to vary the profile of the curve representative of the sedimentation trend if affected by pathologies.

In this regard, it shall be underscored that at specific reading moments M1, M2, M3, the individual sedimentation trends A1, A2, A3 follow profiles that are different from one another.

In such moments M1, M2, M3, therefore, a different behaviour is recorded with respect to the steps of aggregation and falling of the corpuscular components 1a.

The curve of each blood sample 1 is plotted by means of suitable management software, which can be integrated into an erythrocyte sedimentation rate measuring device of the known type as summarily described above.

Advantageously, the sedimentation trend A1, A2, A3 detected for each blood sample is compared with at least one reference parameter representative of at least a given pathology. This reference parameter is represented by a reference sedimentation trend P1, P2, P3 of one or more pathologies.

The comparison is made by detecting whether the sedimentation trend A1, A2, A3 has peculiar characteristics that are likenable (sometimes equal) to the reference sedimentation trend P1, P2, P3. In other words, the moments M1, M2 and M3 (representative of the peculiar characteristics) are compared with the moments present in the reference curves.

Preferably, the comparison step is carried out with a plurality of reference parameters, each of which represented by a reference sedimentation trend P1, P2, P3 of a specific pathology or specific group of pathologies.

In this case as well, in order to simplify the comparison step, the reference sedimentation trends P1, P2, P3 are represented by reference curves. Consequently, the step of comparing the sedimentation trends A1, A2, A3 is carried out by comparing each curve associated with the sedimentation trend A1, A2, A3 with a plurality of reference curves.

In this manner, by verifying the similarity of such curves (measured curve and reference curve) it is possible to establish a specific pathology or a specific group of pathologies for each sedimentation trend A1, A2, A3. A specific result is thus given with respect to the pathology of each blood sample 1 that is analyzed.

Advantageously, the comparison can also be made by observing only specific moments M1, M2, M3 (FIG. 2) that occur in the curve. If such moments M1, M2, M3 correspond to respective reference moments, it will be possible to determine the specific pathology of the blood sample 1.

This situation is given by the fact that, as specified above, at the moments M1, M2, M3 the curves exhibit a very different behaviour in the steps of aggregation of the corpuscular components 1a.

Preferably, the comparison between the sedimentation trend A1, A2, A3 and at least one reference parameter is made by an electronic processing unit integrated with the device for measuring the sedimentation rate. Furthermore, it should be specified that the above-described method of analysis of the present invention has advantageous application if repeated with different blood samples of the same subject. In this case, it will be possible to monitor a predefined pathology, the course thereof during a treatment therapy, or the health conditions of the subject in general.

In this situation, a series of samples are taken at different times within a predefined period, which is determined based on the pathology or health conditions to be monitored.

For example, to verify whether a therapy is working properly, it may be provided for blood samples (which are analyzed according to the above-described method) to be taken at given intervals of time falling within the period in which the treatment is implemented. The performance and effectiveness of the treatment can thus be kept monitored and timely intervention can be undertaken to correct the treatment if necessary.

The present invention thus solves the problems of the prior art and has numerous advantages.

First, it should be noted that the above-described method enables specific indications to be provided as to the presence of a given pathology or group of pathologies, in a simple, fast manner and at very modest costs. This advantage is given by the fact that use is not made of complicated and costly laboratory instruments used only by specialized personnel in a laboratory setting.

The method of the present invention can be carried out with very simple machinery, also usable by non-specialized personnel, since it is based on a direct comparison between measured values (curves representing the sedimentation trend) and reference values.

Such machinery, e.g. devices for measuring the erythrocyte sedimentation rate (ESR), is known to be simple, low-cost, and capable of providing results in a very short time.

In other words, the above-described method is implemented with a test (ESR) that is typically non-specific but which enables specific information to be given, based on a comparison of sedimentation trends, as to the presence and type of pathologies in the blood sample.

Consequently, the method provides such specific information without there being any need to analyze the composition of the blood and thus with considerable savings in the costs of carrying out laboratory analyses.

The invention claimed is:

1. A method for analyzing a blood sample, comprising the steps of:

preparing a blood sample within a respective container;

preventing coagulation of said blood sample by adding an anticoagulant reagent in the blood sample; and measuring a rate at which corpuscular components contained in the blood sample sediment on a bottom of said container, said rate being measured over a predetermined time period;

detecting, within said time period, a sedimentation trend representative of steps of aggregation of the corpuscular components; and comparing the detected sedimentation trend with at least one reference parameter representative of at least one given pathology; said at least one reference parameter is represented by at least one reference sedimentation trend for one or more pathologies;

wherein the step of comparing the sedimentation trend is implemented by determining whether said sedimentation trend has characteristics identical to those of said at least one reference sedimentation trend; wherein said sedimentation trend and said at least one reference sedimentation trend are determined by reading, at a first number of reading moments during the time period, a formation of agglomerates of corpuscular components and a fall thereof in plasma contained in the blood sample; and wherein the step of comparing the sedimentation trend is carried out by comparing the detected sedimentation trend with the at least one reference sedimentation trend at only a second number of specific reference moments corresponding to a sub-selection of said reading moments, the second number being less than the first number.

2. The method according to claim 1, wherein the detected sedimentation trend is compared with a plurality of reference parameters, each of which is represented by a reference sedimentation trend for a specific pathology or a specific group of pathologies.

3. The method according to claim 1, wherein said sedimentation trend is represented by a curve obtained by reading the formation of agglomerates and the fall thereof in the plasma for each moment that elapses sequentially along the time period; said moments being predetermined time intervals.

4. The method according to claim 3, wherein reference parameters are represented by reference curves; said step of comparing the sedimentation trend being carried out by comparing the curve of said sedimentation trend with a plurality of reference curves.

5. The method according to claim 1, wherein it further comprises the step of comparing the measured sedimentation rate with a rate indicative of whether or not a pathology is present.

6. The method according to claim 1, wherein at least said step of comparing the sedimentation trend with at least one reference parameter is carried out by an electronic processing unit.

7. The method according to claim 1, wherein said steps of measuring the sedimentation rate and of detecting the sedimentation trend are carried out by an electronic device for measuring erythrocyte sedimentation rate.

8. The method according to claim 1, wherein the step of comparing the sedimentation trend is carried out by extracting, for each of the reference moments, a value of the detected sedimentation rate from the detected sedimentation trend and at least one value of reference sedimentation rate from the at least one reference sedimentation trend, and by comparing, for each of the reference moments, the value of detected sedimentation rate with the at least one value of reference sedimentation rate.

\* \* \* \* \*